US00PP36881P2

(12) United States Plant Patent
Keil

(10) Patent No.: US PP36,881 P2
(45) Date of Patent: Aug. 5, 2025

(54) ***PHILODENDRON* PLANT NAMED 'EM0003'**

(50) Latin Name: *Philodendron erubescens*
Varietal Denomination: EM0003

(71) Applicant: EMMA'S GARDEN GROWERS, INC., Huntington, NY (US)

(72) Inventor: Jeffrey Keil, Huntington, NY (US)

(73) Assignee: Emma's Garden Growers, Inc., Huntington, NY (US)

( * ) Notice: Subject to any disclaimer, the term of this patent is extended or adjusted under 35 U.S.C. 154(b) by 0 days.

(21) Appl. No.: 18/978,314

(22) Filed: Dec. 12, 2024

(51) Int. Cl.
*A01H 5/12* (2018.01)
*A01H 6/10* (2018.01)

(52) U.S. Cl.
USPC ..... Plt./381
CPC ..... *A01H 6/10* (2018.05)

(58) Field of Classification Search
USPC ..... Plt./381
See application file for complete search history.

*Primary Examiner* — Susan McCormick Ewoldt
(74) *Attorney, Agent, or Firm* — James R. Holm; Plant Novelty Rights, LLC

(57) ABSTRACT

A new and distinct *Philodendron* plant named 'EM0003' particularly distinguished by prolific branching due to a lack of apical dominance, very dense, compact growth habit and flattened globular plant form, consistent leaf color distribution and color patterning across the leaf's upper surface, and more white variegated leaf color compared to the parent plant 'Pink Princess'.

3 Drawing Sheets

Genus and species: *Philodendron erubescens.*
Variety denomination: 'EM0003'.

BACKGROUND OF THE NEW PLANT

The present invention comprises a new and distinct variety of *Philodendron* plant, botanically known as *Philodendron erubescens*, and hereinafter referred to by the variety name 'EM0003'.

This new *Philodendron* plant was discovered by the inventor as a naturally occurring whole-branch mutation of the *Philodendron* plant named 'Pink Princess' (unpatented). The discovery of the new plant was made by the inventor in August 2020 in a non-publicly accessible area of a commercial greenhouse located in Suffolk County, New York. 'EM0003' was selected by the inventor due to its greater branching tendencies, its flattened globular plant shape and for the presence of white leaf variegation.

'EM0003' was first reproduced asexually using vegetative tip cuttings in Suffolk County, New York in the summer of 2021. Asexual propagation by vegetative tip cuttings of the new variety has shown that the unique features of the new variety are stable and reproduced true-to-type to date through approximately 5 successive generations.

Plant Breeder's Rights for this variety have not been applied for. 'EM0003' has not been made publicly available or sold anywhere in the world more than one-year prior to the effective filing date of this application.

SUMMARY OF THE INVENTION

The new *Philodendron* variety has not been observed under all possible environmental conditions. The phenotype may vary somewhat with variations in environment such as temperature, day length, light intensity, water status, fertilizer rate and type, without, however, any variance in genotype.

The following are the most outstanding and distinguishing characteristics of this new *Philodendron* variety. The combination of these characteristics distinguishes 'EM0003' as a new and distinct variety of *Philodendron:*

1. Prolific branching due to a lack of apical dominance.
2. Very dense, compact growth habit and flattened globular plant form.
3. Consistent leaf color distribution and color patterning across the leaf's upper surface.
4. More white variegated leaf color compared to the parent plant 'Pink Princess'.

DESCRIPTION OF THE PHOTOGRAPHS

This new *Philodendron* variety is illustrated by the accompanying-colored photographs which show the overall appearance and distinct characteristics of the plant. The colors shown are as true as can be reasonably obtained by conventional photographic procedures. Colors in the photographs may differ slightly from the color values cited in the botanical description which accurately describes the colors of the new variety.

Figure 1:
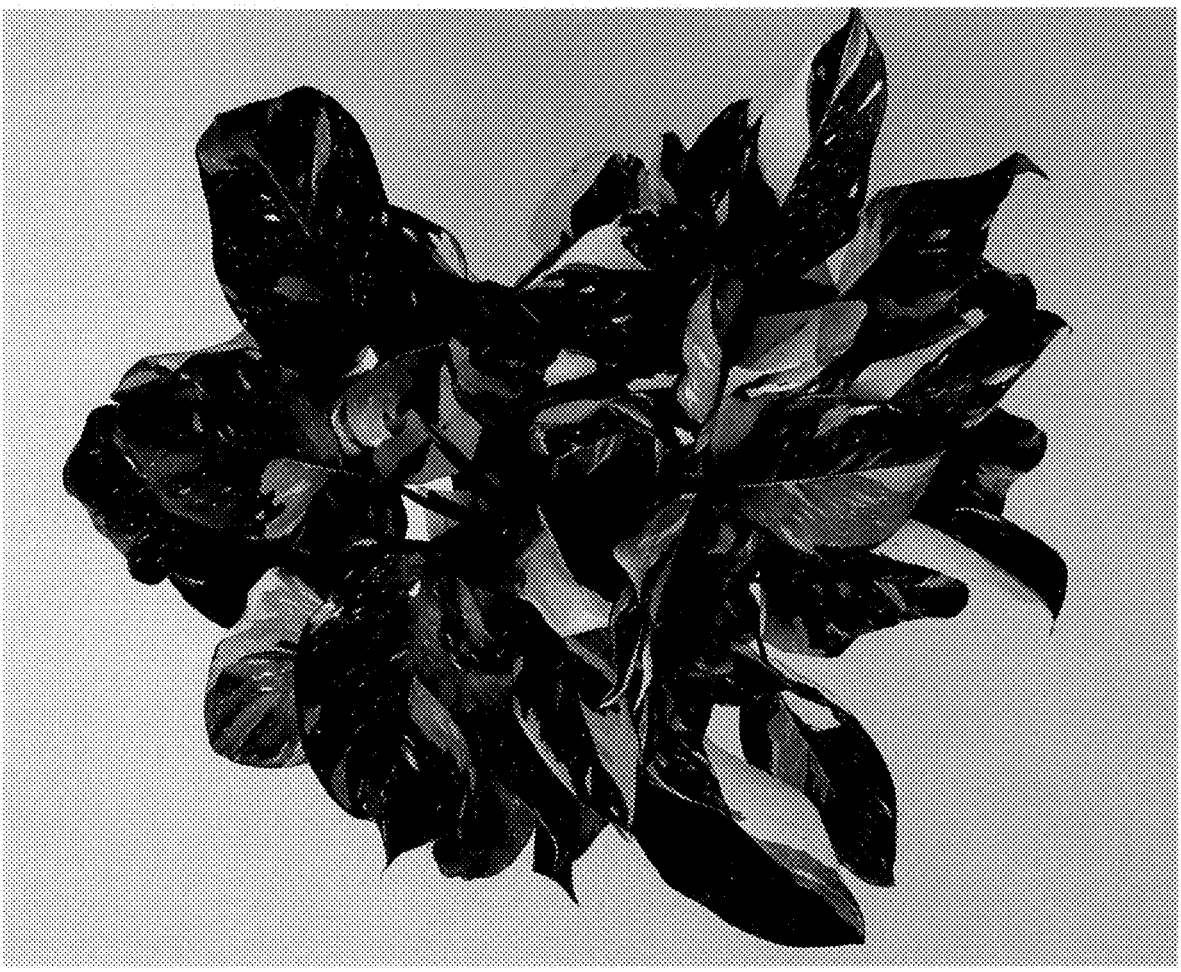

FIG. 1. Shows an overhead view of the overall plant form and foliage of 'EM0003'.

Figure 2:
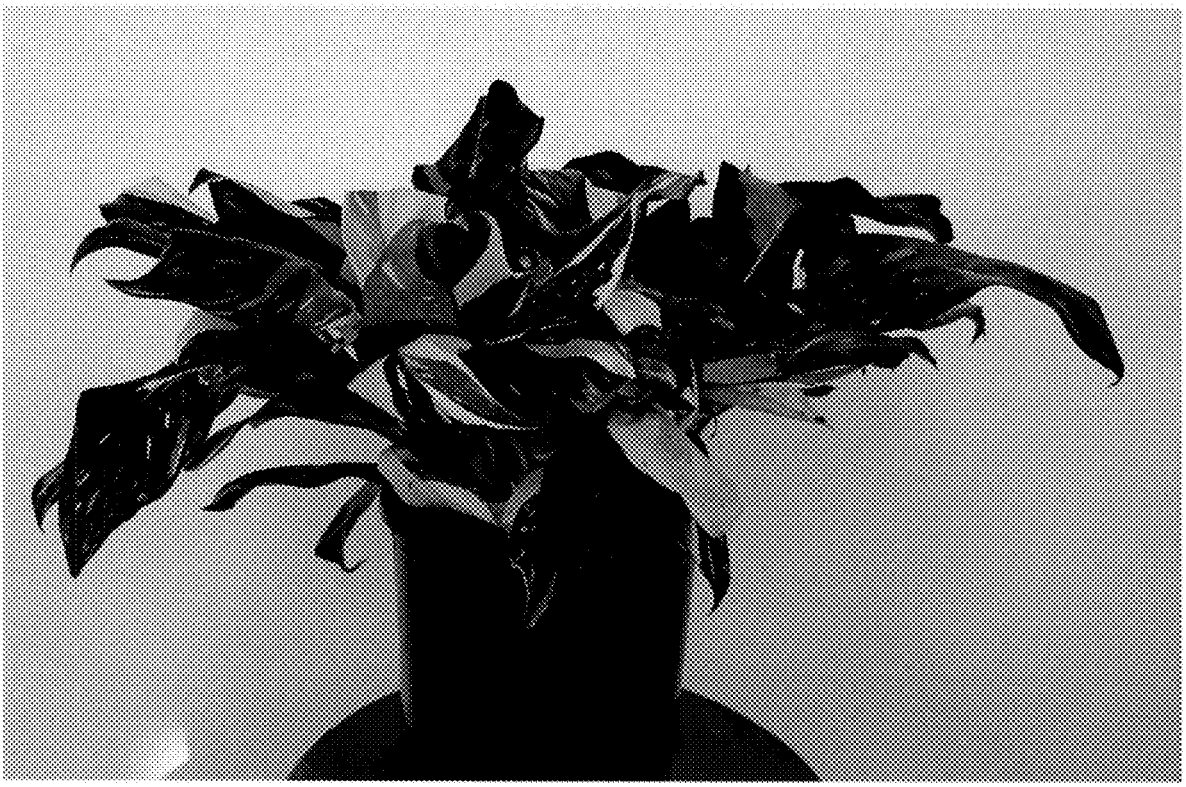

FIG. 2. Shows a side view of the overall plant form and foliage of 'EM0003'.

Figure 3:
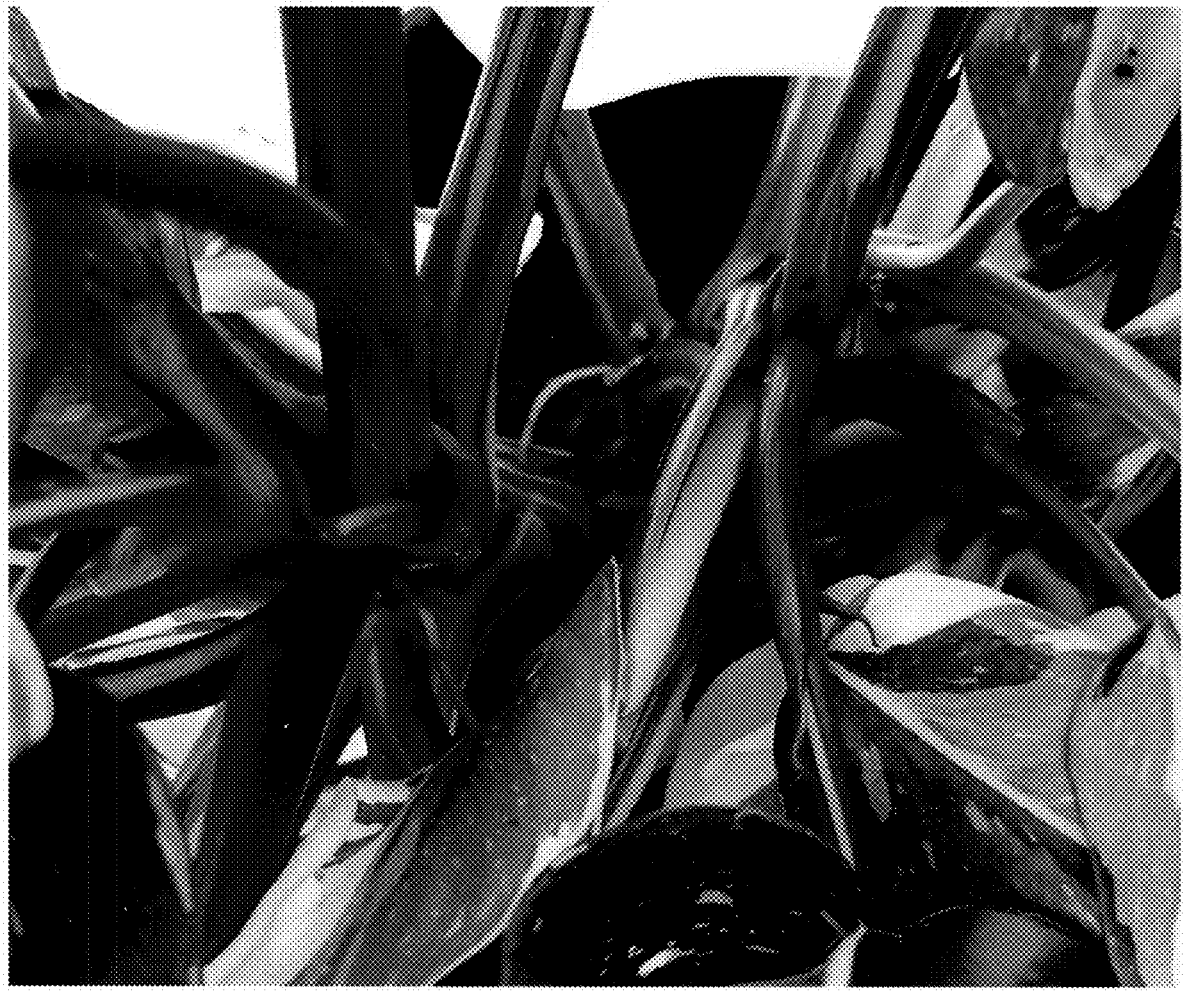

FIG. 3. Shows a close-up view of the inner crowns of 'EM0003'.

DESCRIPTION OF THE NEW VARIETY

In the following description, color references are made to The Royal Horticultural Society Colour Chart, Sixth Edition, except where general color terms of ordinary dictionary significance are used. The following observations and measurements describe plants grown under moderate shade in a glass covered greenhouse in Suffolk County, New York with an average temperature of 75° F. Detailed descriptions and photographs were taken in December 2023 from 1-year-old plants grown in 1-gallon containers. Measurements and numerical values represent averages of typical plant types. Leaf color designations and the size and position of the color patches in the forthcoming examples describe typical leaves observed on plants of 'EM0003' but are not meant to be exhaustive of all variations of leaf color patterning observed on plants of 'EM0003'.

DETAILED BOTANICAL DESCRIPTION

Classification:

*Family*.—Araceae.

*Botanical*.—*Philodendron erubescens*.

*Common*.—*Philodendron*.

*Denomination*.—'EM0003'.

General description:

*Plant type*.—Herbaceous tropical perennial.

*Plant shape*.—Flattened globular.

*Growth habit*.—Upright and compact, very dense growth habit.

*Plant height from soil level to top of foliar plane*.—18.0 cm.

*Plant width*.—Approximately 45.0 cm to 48.0 cm.

*Growth rate*.—Moderate to fast, contingent on favorable growing conditions.

*Branching characteristics*.—Freely branching with approximately 8 to 9 primary branches and 3 to 5 secondary branches with no central dominant branch.

*Primary branch length*.—Approximately 10.0 cm to 15.0 cm.

*Primary branch diameter*.—Approximately 1.0 cm at the base, widening to 1.8 cm mid-branch.

*Internode length*.—Approximately 1.0 cm to 1.3 cm.

*Texture of branches*.—Smooth.

*Branch color*.—Branch color is generally not visible as the petiole wings clasp the branch.

*Number of leaves per primary branch*.—About 10 to 12.

*Propagation type*.—Vegetative tip cuttings.

*Time to produce a rooted cutting*.—Approximately 4 to 6 weeks.

Foliage description:

*Arrangement*.—Alternate to whorled.

*Attachment*.—Petiolate.

*Leaf*.—Shape: Ovate to slightly cordate. Length: Approximately 12.0 to 15.0 cm. Width: Approximately 5.0 cm to 10.0 cm. Aspect: Moderately concave. Apex shape: Acuminate and curved. Base shape: Truncate with some cordate tendencies. Texture and sheen (both upper and lower surfaces): Leathery and glossy. Orientation: Newly unfurled leaves are held angular upright, mature leaves are held horizontal and then slightly downwards as branch growth progresses. Margins: Entire. Color: Variegated, irregular sized patches and streaks of coloration; the examples below are typical of leaves observed on plants of 'EM0003'. Example 1: Adaxial surface: Primarily 139A (dark yellowish green); large streaks of 191A (greyish yellow green); and small streaks of N155B (pinkish white). Abaxial surface: Primarily 146B (moderate yellow green); large streaks of N155A (bluish white) which are slightly tinted with 186D (moderate purplish pink) and N155B (pinkish white); and slight streaks of 186A (moderate purplish red) near and along the leaf margin. Example 2:Adaxial surface: One side of the leaf blade from the midrib colored NN155D (white) with streaks of 191A (greyish yellow green); and the opposite side of the leaf blade from the midrib colored 139A (dark yellowish green) with slight streaking of 191A (greyish yellow green). Abaxial surface: One side of the leaf blade from the midrib colored 146B (moderate yellow green) with slight streaks of 186A (moderate purplish red) near and along the leaf margin; and the opposite side of the leaf blade from the midrib colored NN155D (white) with streaks of 191A (greyish yellow green). Example 3: Adaxial surface: Approximately two-thirds of the surface colored N189A (dark greyish green) with a broad streak of 141B (deep yellowish green), several streaks of 190B to 190C (pale green and light greenish grey) tinted with slight 186C (dark purplish pink); and approximately one-third of the surface colored 190B to 190C (pale green and light greenish grey) tinted with slight 186C (dark purplish pink) and some NN155B (pinkish white). Abaxial surface: Primarily 146D (moderate yellow green) and strongly tinted with 186C (moderate purplish red); large streaks of 190B to 190C (pale green and light greenish grey); smaller streaks and flecks of 186A to 186B (moderate purplish red); and some NN155D (white) along the margins of the lower lobes. Example 4: Adaxial surface: One side of the leaf blade from the midrib colored primarily 139A (dark yellowish green) with streaks and flecks of 191D (light greenish grey) and NN155D (white); and the opposite side of the leaf blade from the midrib colored primarily 191A (light greenish grey) with streaks of 156D (yellowish white) and a patch of 139A (dark yellowish green) along the margin. Abaxial surface: Primarily colored 146D (moderate yellow green) mixed with faint streaks of 186A to 186B (moderate purplish red), 191D (light greenish grey) and NN155D (white). Venation: Pattern: Arcuate. Color: Upper surface: 147A (moderate olive green). Lower surface: 186A to 186B (moderate purplish red).

*Petiole*.—Length: Approximately 10.0 cm to 13.0 cm. Width: Approximately 1.0 cm to 1.5 cm at the position of attachment to the branch and 0.3 cm to 0.5 cm at the position of attachment to the leaf blade. Color (both outer and inner surfaces, including petiole wings): Variable, predominately colored 187A (dark red) with stripes and tints of 148A (moderate olive green) and stripes and tints of NN155D (yellowish white). Petiole wings: Shape: Deltoid. Length: Approximately 0.5 cm to 0.9 cm. Width: Approximately 1.0 cm to 1.5 cm.

*Aerial roots*.—One aerial root nodule present at each node, approximately 0.64 cm to 1.27 cm in length and colored 166A (greyish brown).

Inflorescence: None observed.

Cold tolerance: None observed.

Drought tolerance: None observed.
Disease and pest tolerance: None observed.
Fruit and seed set: None observed.

COMPARISON WITH PARENTAL VARIETY

'EM0003' differs from the parent *Philodendron* plant 'Pink Princess' in that 'EM0003' has leaves with predominately white colored variegation, whereas 'Pink Princess' has leaves with predominately pink colored variegation. Additionally, 'EM0003' has reduced apical dominance with more branching tendencies, whereas 'Pink Princess' has greater apical dominance and less branching tendencies.

COMPARISON WITH COMMERCIAL VARIETY

'EM0003' differs from the commercial *Philodendron* plant 'White Knight' (unpatented) in that 'EM0003' has more consistent white leaf variegation patterns compared to 'White Knight'. Additionally, 'EM0003' has reduced apical dominance with more branching tendencies, whereas 'White Knight' has greater apical dominance and less branching tendencies.

I claim:

1. A new and distinct variety of *Philodendron* plant named 'EM0003', substantially as illustrated and described herein.

* * * * *